United States Patent
Newsome

(10) Patent No.: US 11,788,959 B1
(45) Date of Patent: Oct. 17, 2023

(54) LIGHTING APPARATUS WITH FILTER HAVING IMPROVED TRANSMISSIVITY, IMPROVED SOLARIZATION RATE, OR BOTH IMPROVED TRANSMISSIVITY AND IMPROVED SOLARIZATION RATE

(71) Applicant: UV SYSTEMS, Inc., Renton, WA (US)

(72) Inventor: Donald E. Newsome, Renton, WA (US)

(73) Assignee: UV SYSTEMS, Inc., Renton, WA (US)

( * ) Notice: Subject to any disclaimer, the term of this patent is extended or adjusted under 35 U.S.C. 154(b) by 0 days.

(21) Appl. No.: 18/184,311

(22) Filed: Mar. 15, 2023

Related U.S. Application Data

(60) Provisional application No. 63/427,578, filed on Nov. 23, 2022.

(51) Int. Cl.
| | |
|---|---|
| *G01N 21/64* | (2006.01) |
| *G01N 33/24* | (2006.01) |
| *E21B 49/00* | (2006.01) |
| *E21C 39/00* | (2006.01) |

(52) U.S. Cl.
CPC ............ *G01N 21/64* (2013.01); *G01N 33/24* (2013.01); *E21B 49/005* (2013.01); *E21C 39/00* (2013.01)

(58) Field of Classification Search
CPC ...... G01N 21/64; G01N 33/24; E21B 49/005; E21C 39/00
See application file for complete search history.

(56) References Cited

U.S. PATENT DOCUMENTS

| | | | | |
|---|---|---|---|---|
| 5,175,437 | A | * | 12/1992 | Waluszko ............... F21V 19/04 250/492.1 |
| 6,911,657 | B2 | | 6/2005 | Waluszko |
| 9,961,927 | B2 | | 5/2018 | Garrett |
| 11,243,170 | B2 | | 2/2022 | Zhu et al. |
| 2016/0282281 | A1 | | 9/2016 | Fujitani |
| 2019/0099508 | A1 | | 4/2019 | Garrett |
| 2022/0177353 | A1 | | 6/2022 | Kruger et al. |

FOREIGN PATENT DOCUMENTS

| | | |
|---|---|---|
| JP | H1110101 A | 1/1999 |
| TW | 200930140 A | 7/2009 |

* cited by examiner

*Primary Examiner* — David P Porta
*Assistant Examiner* — Meenakshi S Sahu
(74) *Attorney, Agent, or Firm* — Volpe Koenig

(57) ABSTRACT

In an embodiment, a lighting apparatus includes a housing, a lamp, and a filter. The housing has a cavity with an opening, and the lamp is disposed within the cavity and is configured to emit electromagnetic radiation at wavelengths of approximately 253.7 nanometers and of approximately 405 nanometers. And the filter is mounted adjacent to the opening and is configured to pass the emitted electromagnetic radiation at the wavelength of approximately 253.7 nanometers with a transmissivity of at least approximately 70% and at the wavelength of approximately 405 nanometers with a transmissivity of no more than approximately 5%.

22 Claims, 12 Drawing Sheets

2000

US 11,788,959 B1

LIGHTING APPARATUS WITH FILTER HAVING IMPROVED TRANSMISSIVITY, IMPROVED SOLARIZATION RATE, OR BOTH IMPROVED TRANSMISSIVITY AND IMPROVED SOLARIZATION RATE

CROSS REFERENCE TO RELATED APPLICATION

This application claims the benefit of 63/427,578 filed Nov. 23, 2022, which is incorporated by reference as if fully set forth.

SUMMARY

An embodiment of a lighting apparatus includes a housing, a lamp, and a filter. The housing has a cavity with an opening, and the lamp is disposed within the cavity and is configured to emit electromagnetic radiation at wavelengths of approximately 253.7 nanometers and of approximately 405 nanometers. And the filter is mounted adjacent to the opening and is configured to pass the emitted electromagnetic radiation at the wavelength of approximately 253.7 nanometers with a transmissivity of at least approximately 70% and at the wavelength of approximately 405 nanometers with a transmissivity of no more than approximately 5%.

Another embodiment of the lighting apparatus is similar to the preceding embodiment but the lamp is also configured to emit electromagnetic radiation at approximately 306 nanometers, 312 nanometers, and 365 nanometers, and the filter is also configured to pass the emitted electromagnetic radiation at one or more of the wavelengths of approximately 306 nanometers, 312 nanometers, and 365 nanometers with respective transmissivities of at least approximately 70%.

As compared to other lights and lighting apparatuses, such a lighting apparatus can have a significantly higher transmissivity (i.e., a lower attenuation) at one or more UV wavelengths, such as approximately one or more of the following wavelengths: 253.7 nanometers, 306 nanometers, 312 nanometers, and 365 nanometers (some or all of which can be radiated by the lighting apparatus), a significantly lower transmissivity (i.e., a higher attenuation) at visible wavelengths, such as approximately 405 nanometers (which can be radiated by the lamp of the lighting apparatus), and a significantly slower rate of solarization. For example, such a lighting apparatus can have a transmissivity of at least approximately 70% (for example, more than approximately 65%, more than approximately 70%, more than approximately 75%, more than approximately 80%, or more than approximately 82.5%) at one or more of the following wavelengths: approximately 253.7 nanometers, approximately 306 nanometers, approximately 312 nanometers, and approximately 365 nanometers, and can have a transmissivity of no more than approximately 5% (for example, no more than approximately 4%, no more than approximately 3%, no more than approximately 2%, no more than approximately 1%, or no more than approximately 0.5%) at approximately 405 nanometers.

Such a lighting apparatus can be used, for example, to fluoresce one or more fluorescent minerals (e.g., —willemite) with ultraviolet light at one or more of the following wavelengths: approximately 253.7 nanometers, approximately 306 nanometers, approximately 312 nanometers, and approximately 365 nanometers, thus causing the fluorescent mineral(s) to fluoresce. Because visible light from a source (e.g., the lighting apparatus) other than the fluorescing minerals themselves can degrade, e.g., the intensity, contrast, and color of a fluorescing mineral as perceived by the human eye, the filter of the lighting apparatus is configured to attenuate visible light (e.g., at 405 nanometers and 435 nanometers) radiating from the lighting apparatus.

Applications of such a lighting apparatus include fluorescing oil-well drill cuttings and cores (fluorescing minerals in the cuttings and cores can indicate the thermal maturity of the oil), fluorescing walls and other rocks in underground mines (fluorescing minerals in the walls and other rocks can facilitate the identifying and tracing of ore-bearing rocks), fluorescing rocks on picking lines (fluorescing minerals can facilitate the spotting of valuable pieces of ore), fluorescing rocks discovered by prospectors and hobbyists to indicate whether the rocks contain one or more fluorescent minerals, and fluorescing fluorescent minerals in a fluorescent-mineral display.

BRIEF DESCRIPTION OF THE DRAWINGS

A more detailed understanding may be had from the following description, given by way of example in conjunction with the accompanying drawings, wherein like reference numerals in the figures indicate like elements, and wherein.

DETAILED DESCRIPTION

In the following description, "approximately," "approximately," "about," and "substantially" mean that a quantity (e.g., a length, a wavelength) can vary from a given value (e.g., 254 nanometers) by up to ±20% (e.g., ±20% of 254 nanometers=50.8 nanometers, which means an "approximate" value of 254 nanometers can range from 254−50.8=203.2 nanometers to 254+50.8 nanometers=304.8 nanometers), which range includes exactly 253.7 nanometers and exactly 254 nanometers.

Figure 1:
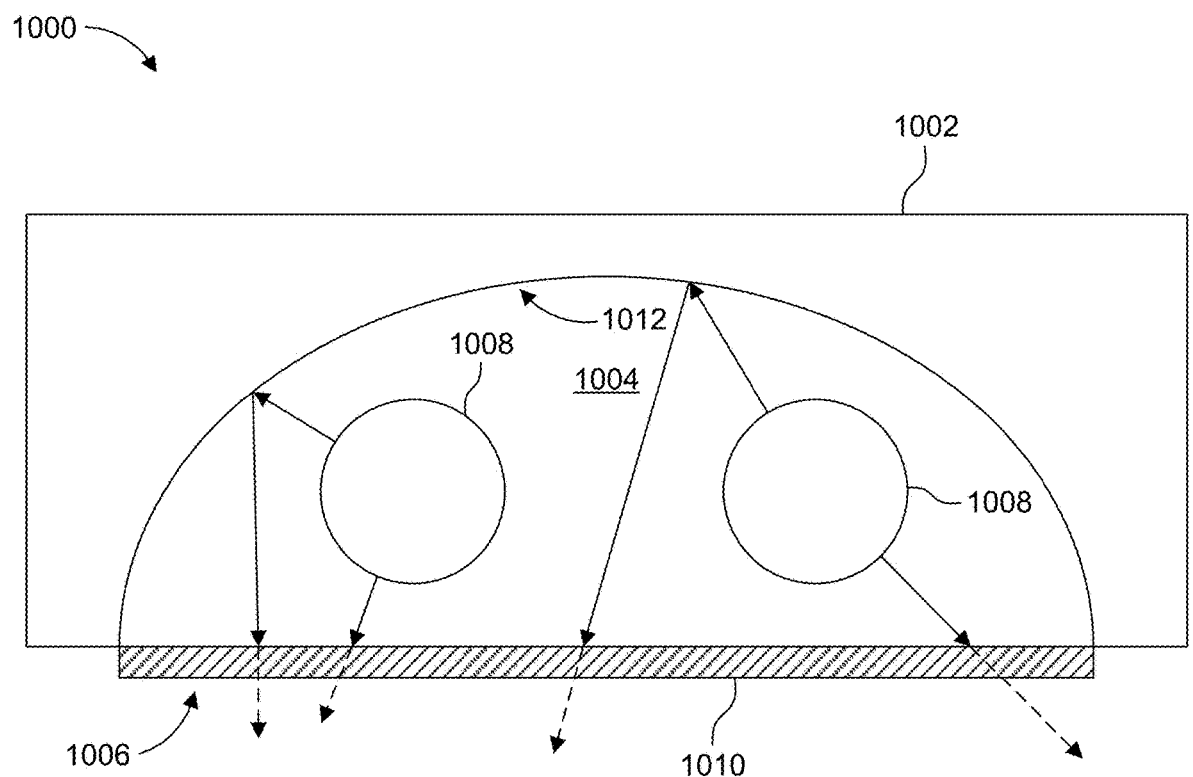
FIG. 1 is a cross section of a lighting apparatus.

FIG. 1 is a cross-sectional view of an end of a lighting apparatus 1000, which includes a housing 1002, a cavity 1004 having an opening 1006, a lamp 1008 disposed in the cavity, and a filter 1010, which spans the opening of the cavity, according to an embodiment. Other not-shown components of the lighting apparatus 1000 include a power-supply connector and a power supply configured to power the lamp 1008, and circuitry such as a ballast to drive the lamp.

The housing 1002 can be made from any suitable material such as one or more metals, and can be coated with paint or any other suitable coating.

The cavity 1004 can have any suitable cross-sectional shape such as semicircular or parabolic, and has an inside wall 1012, which can be coated with a reflective material such as aluminum, glass, a Bragg reflector, or other reflective material.

The lamp 1008 can be any suitable type of lamp such as a mercury arc lamp or a light-emitting diode (LED) such as IBT LB3535-UV-C-2D2-255. Other types of ultraviolet lamps, such as a UV fluorescent light, can be used, although compared to a mercury arc lamp and an LED, the other types of ultraviolet lamps can have problems such as generating one or more wavelengths (e.g., 185 nanometers) that, in turn, generate a noticeable level of ozone. Noticeable levels of ozone can be undesirable because, e.g., the ozone has an odor that many people find unpleasant and the ozone (for example, in combination with exposure to ultraviolet light at, e.g., approximately 185 nanometers and approximately 253.7 nanometers) can accelerate degradation of components and materials inside of the lighting apparatus 1000.

And the filter 1010 is a colored glass optical filter, for example, an ultraviolet-transmitting, visible-absorbing filter such as a filter U325C manufactured by the Hoya Corporation.

Figure 2:
FIG. 2 is a rendition of a fluorescent display of fluorescent minerals.

It is known that fluorescing one or more fluorescent minerals with electromagnetic radiation at one or more of the following wavelengths: approximately 253.7 nanometers (sometimes rounded to 254 nanometers), approximately 306 nanometers, approximately 312 nanometers, and approximately 365 nanometers, causes the fluorescent minerals to fluoresce, that is, to generate visible wavelengths of light, in a manner that renders the fluorescing minerals colored and appealing to the human eye. FIG. 2 is a fluorescent-mineral display 2000, which illustrates this phenomena.

It is also known that, in general, fluorescing minerals can be more colorful and more visually appealing to the human eye when the source of the one or more wavelengths of approximately 253.7 nanometers, approximately 306 nanometers, approximately 312 nanometers, and approximately 365 nanometers, generates little or no visible light. That is, fluorescing minerals typically are more colorful and visually appealing to the human eye when the only visible light emanating from the ultraviolet source and the fluorescing minerals is the visible light being generated by the fluorescing minerals themselves. And to increase the visual appeal to the human eye even more, fluorescent minerals may be fluoresced and displayed in a dark environment in which the visible environmental light (visible environmental light is the visible light other than the visible light being generated by the fluorescing minerals themselves) is significantly reduced in intensity or is eliminated; the FIG. 2 rendition 2000 of a fluorescent-mineral display is an example of the visible environmental light having negligible to zero intensity.

Consequently, the lighting apparatus 1000 would operate, ideally, with the lamp 1008 emitting the dominant wavelength(s) of electromagnetic radiation at one or more of the following wavelengths: approximately 254 nanometers, approximately 306 nanometers, approximately 312 nanometers, and approximately 365 nanometers (so that all of the electromagnetic radiation emitted by the lamp would be used to cause the fluorescent minerals to fluoresce, thus giving the brightest fluorescence for a given power of the emitted electromagnetic radiation) and, therefore, emitting no visible wavelengths of electromagnetic radiation. And the lighting apparatus 1000 would operate, nearly ideally, with the lamp 1008 emitting most of its power at one or more of the following wavelengths: approximately 254 nanometers, approximately 306 nanometers, approximately 312 nanometers, and approximately 365 nanometers, but still emitting no visible wavelengths of electromagnetic radiation.

But the lighting apparatus 1000 typically does not operate in such an ideal, or nearly ideal, manner. In addition to emitting primary ultraviolet radiation at one or more of the following wavelengths: approximately 254 nanometers, approximately 306 nanometers, approximately 312 nanometers, and approximately 365 nanometers, the mercury arc lamp 1008 typically emits one or more other visible wavelengths approximately at 405, 435, 548, 576, and 579 nanometers. As is known, a wavelength approximately of 380 nanometers is considered to be the threshold between shorter, invisible wavelengths of electromagnetic radiation and longer, visible wavelengths of electromagnetic radiation. Consequently, the lamp 1008 emits a significant number of wavelengths (e.g., five wavelengths) of electromagnetic energy that are well within the visible range and that have significant intensities. Sometimes the wavelengths that the lamp 1008 emits are called "emission lines," such that the lamp 1008 emits several emission lines in the visible portion of the electromagnetic spectrum.

Although the intensities of the visible wavelengths generated by the lamp 1008 typically are sometimes lower than the intensities of the visible wavelengths generated by the fluorescing one or more minerals, the intensities of the visible wavelengths generated by the lamp are typically high enough to degrade the visual appeal of a fluorescent-mineral display.

To reduce the degradation of the visual appeal of the fluorescent-mineral display by the lamp 1008, the glass filter 1010 spans the opening 1006 of the cavity 1004 such that the filter is disposed between the lamp 1008 and the one or more fluorescent minerals (not shown in FIG. 1, but see FIG. 2).

Ideally, the filter would pass 100% (i.e., would have a transmissivity of 100% or an attenuation of 0%) of the intensity of at least one of the one or more "good" (invisible) ultraviolet wavelengths (ultraviolet transmission lines) of approximately of 254 nanometers, approximately 306 nanometers, approximately 312 nanometers, and approximately 365 nanometers generated by the lamp 1008, and would pass 0% (i.e., would have a transmissivity of 0% or an attenuation of 100%) at the "bad" (visible) wavelengths generated by the lamp, which, for example, are lamp emission lines at approximately 405, 435, 548, 576, and 579 nanometers.

Unfortunately, when used as the filter 1010, a colored glass ultraviolet-transmitting, visible-absorbing, optical filter, for example, the filter U325C manufactured by the Hoya Corporation, falls far short of this ideal. Furthermore, tuned optical mirrors that effectively attenuate one or more wavelengths and pass another one or more wavelengths also fall far short of this ideal.

Figure 3:
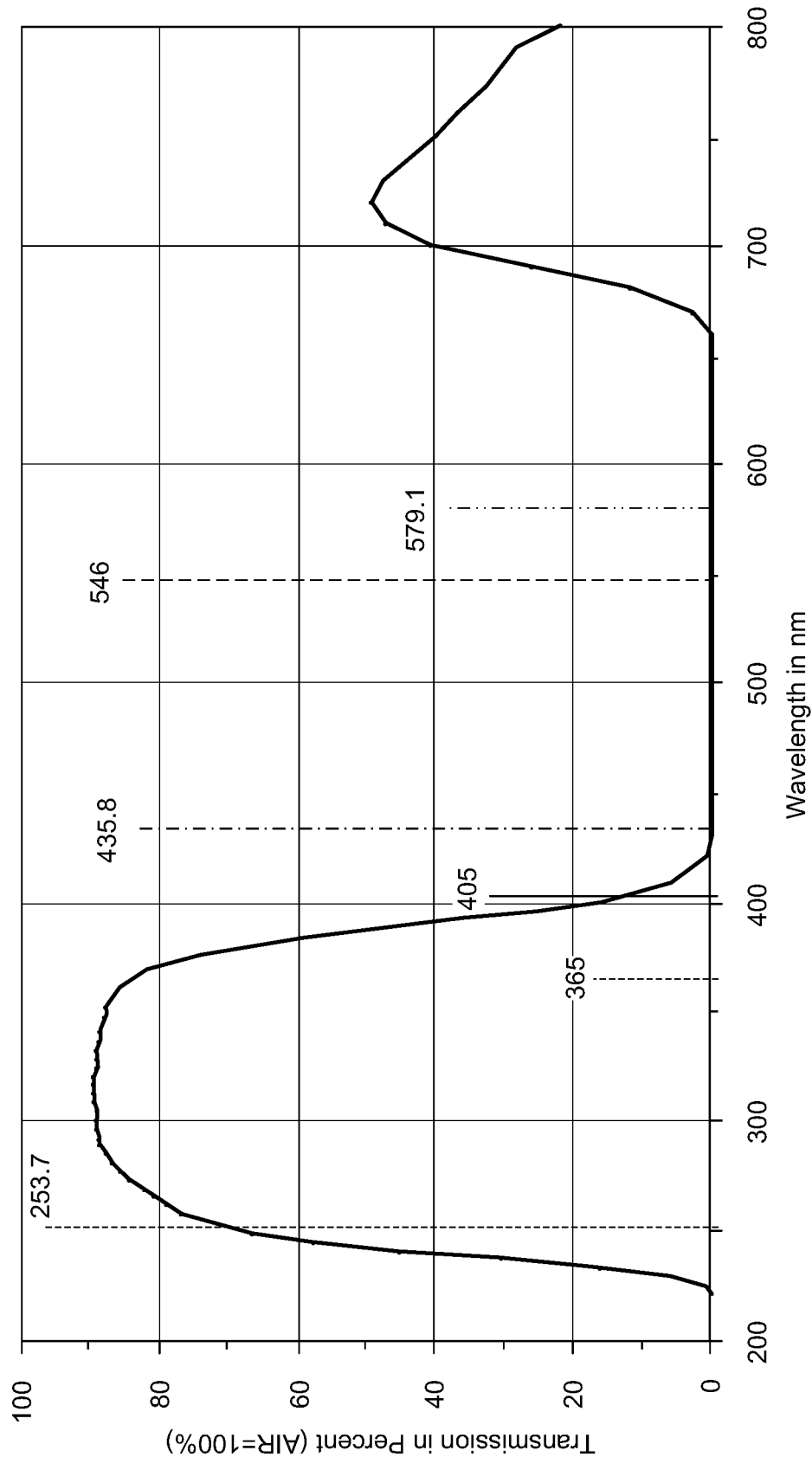
FIG. 3 is a plot of transmissivity versus wavelength for the filter of FIG. 1.

FIG. 3 is a plot of the intensity transmissivity of an optical filter U325C versus wavelength.

One can see that the U325C filters transmissivities at "good" invisible ultraviolet wavelengths of approximately 253.7 nanometers, approximately 306 nanometers, approximately 312 nanometers, and approximately 365 nanometers, are only approximately 60% (this is also evident from the plot of FIG. 8), approximately 88%, approximately 88%, and approximately 85%, respectively, that although the filter's transmissivity at the visible wavelengths of approximately 435, 548, 576, and 579 nanometers is less than 5%, the filter's transmissivity at the visible wavelength of approximately 405 nanometers is significant, at about 15%.

Referring to FIGS. 1-3, another problem with a colored glass ultraviolet-transmitting, visible-absorbing, optical filter, for example, the U325C, is solarization, which is the tendency of the transmissivity of the filter to degrade (become lower) over time with exposure to ultraviolet light, such as ultraviolet light from the lamp 2008 at one or more of the following wavelengths: approximately 254 nanometers, approximately 306 nanometers, approximately 312 nanometers, and approximately 365 nanometers. Although such solarization may result in a favorable reduction of the transmissivities at "bad" visible wavelengths such as 405, 435, 548, 576, and 579 nanometers, such solarization typically results in an unfavorable reduction of the transmissivity at "good" invisible wavelengths such as approximately 254 nanometers, approximately 306 nanometers, approximately 312 nanometers, and approximately 365 nanometers. For example, such a reduction in transmissivity of the filter 1010 over time at one or more of the following wavelengths: approximately 254 nanometers, approximately 306 nanometers, approximately 312 nanometers, and approximately 365 nanometers, may reduce, over time, the intensity at which the minerals in the display 2000 of FIG. 2 fluoresce, and, therefore, may degrade the visual appeal of the fluorescent-mineral display over time.

Figure 4:
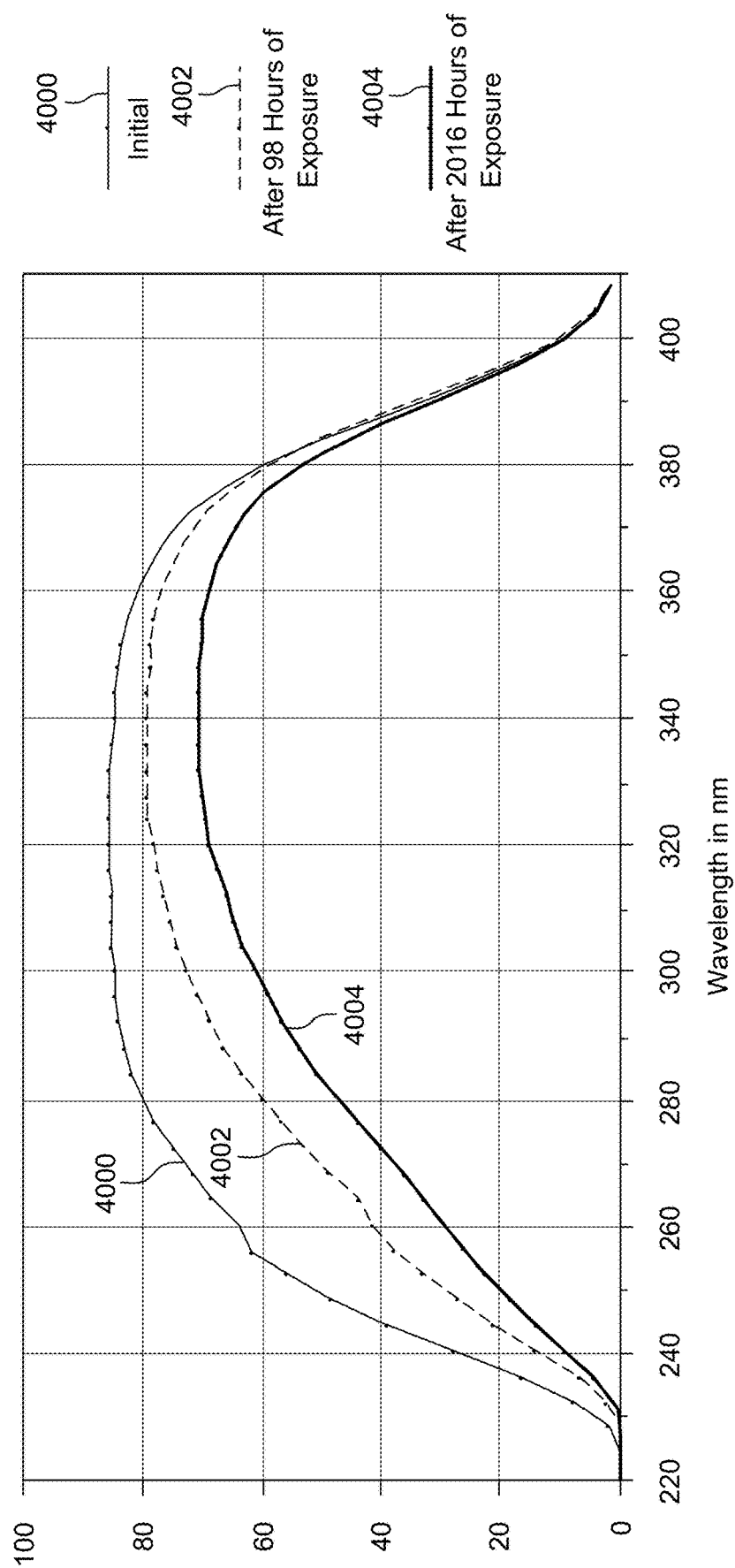
FIG. 4 is a plot of transmissivity versus wavelength for a filter that can be used as the filter of FIG. 1 after respective numbers of hours of exposure of the filter to electromagnetic radiation emitted by the lamp of FIG. 1.

FIG. 4 is a plot of transmissivity versus wavelength for a Kopp Glass #9863 colored glass ultraviolet-transmitting, visible-absorbing, optical filter, after 0 (plot curve 4000), 98 (plot curve 4002), and 2016 (plot curve 4004) hours of exposure to ultraviolet light at approximately 254 nanometers.

Figure 5:
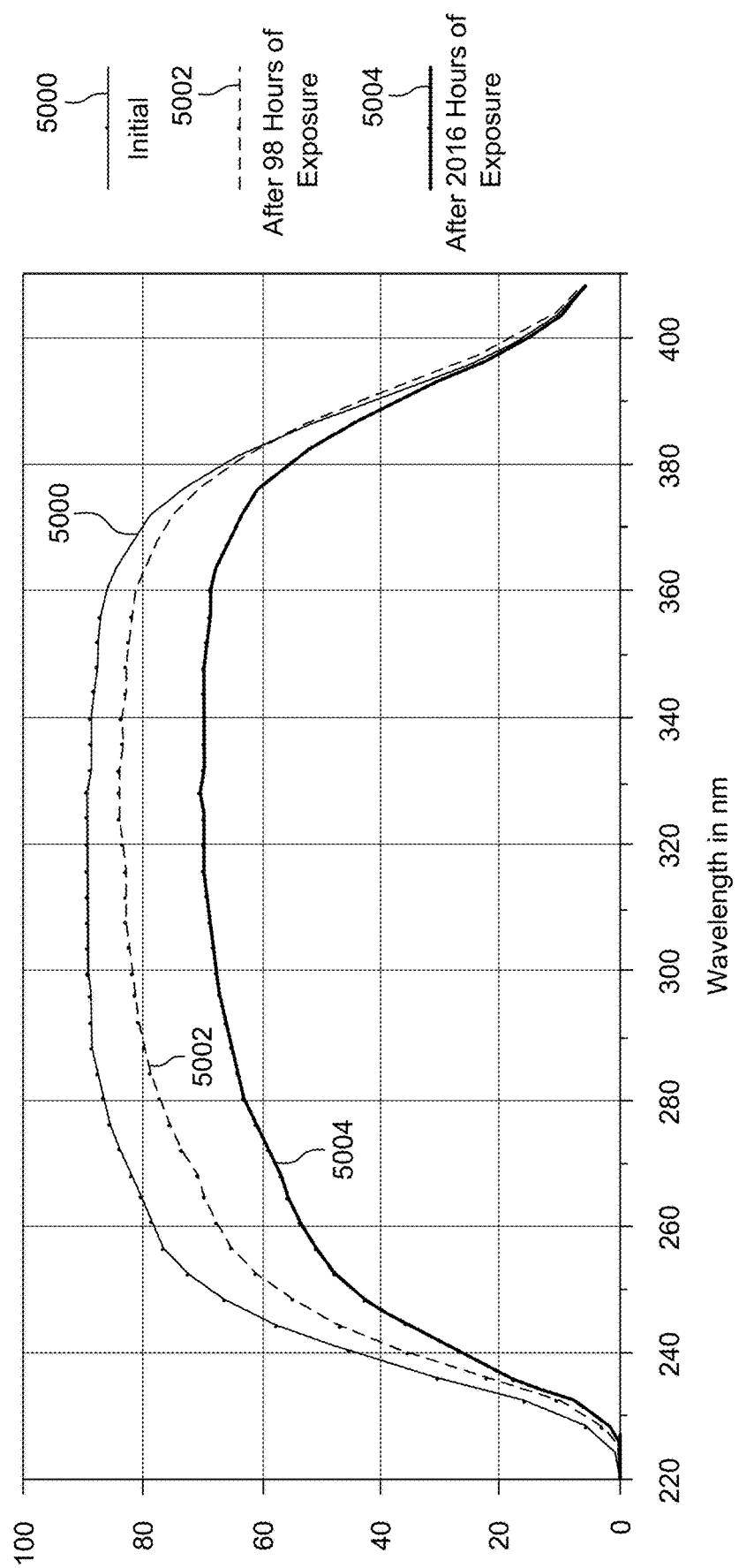
FIG. 5 is a plot of transmissivity versus wavelength of another filter that can be used as the filter of FIG. 1 after respective numbers of hours of exposure of the filter to electromagnetic radiation emitted by the lamp of FIG. 1.

FIG. 5 is a plot of transmissivity versus wavelength for a Hoya U325C colored glass ultraviolet-transmitting, visible-absorbing, optical filter, after 0 (plot curve 5000), 98 (plot curve 5002), and 2016 (plot curve 5004) hours of exposure to ultraviolet light at approximately 254 nanometers.

Referring to FIGS. 4 and 5, one can see that the Kopp and Hoya ultraviolet-glass (UVG) filters experience significant solarization. For example, the Kopp filter experiences a drop in transmissivity at approximately 253.7 nanometers of approximately 30%-40% after only approximately 100 hours of operation (the Kopp filter experiences similar drops in transmissivity at approximately 306 nanometers, approximately 312 nanometers, and approximately 365 nanometers), and the Hoya filter experiences a drop in transmissivity at 253.7 nanometers of approximately 15%-25% after only approximately 100 hours of operation (the Hoya filter experiences similar drops in transmissivity at approximately 306 nanometers, approximately 312 nanometers, and approximately 365 nanometers).

Consequently, there is a need for an optical filter suitable for use in a light apparatus, such as the light apparatus 1000 of FIG. 1, having higher transmissivities (lower attenuations) at one or more wavelengths, such as approximately 253.7 nanometers, approximately 306 nanometers, approximately 312 nanometers, and approximately 365 nanometers, that cause fluorescent minerals to fluoresce, and having lower transmissivities (higher attenuations) at visible wavelengths, particularly visible wavelengths generated by a lamp of a lighting apparatus, such as the lighting apparatus 1000 of FIG. 1, configured to cause fluorescent minerals to fluoresce.

Figure 6:
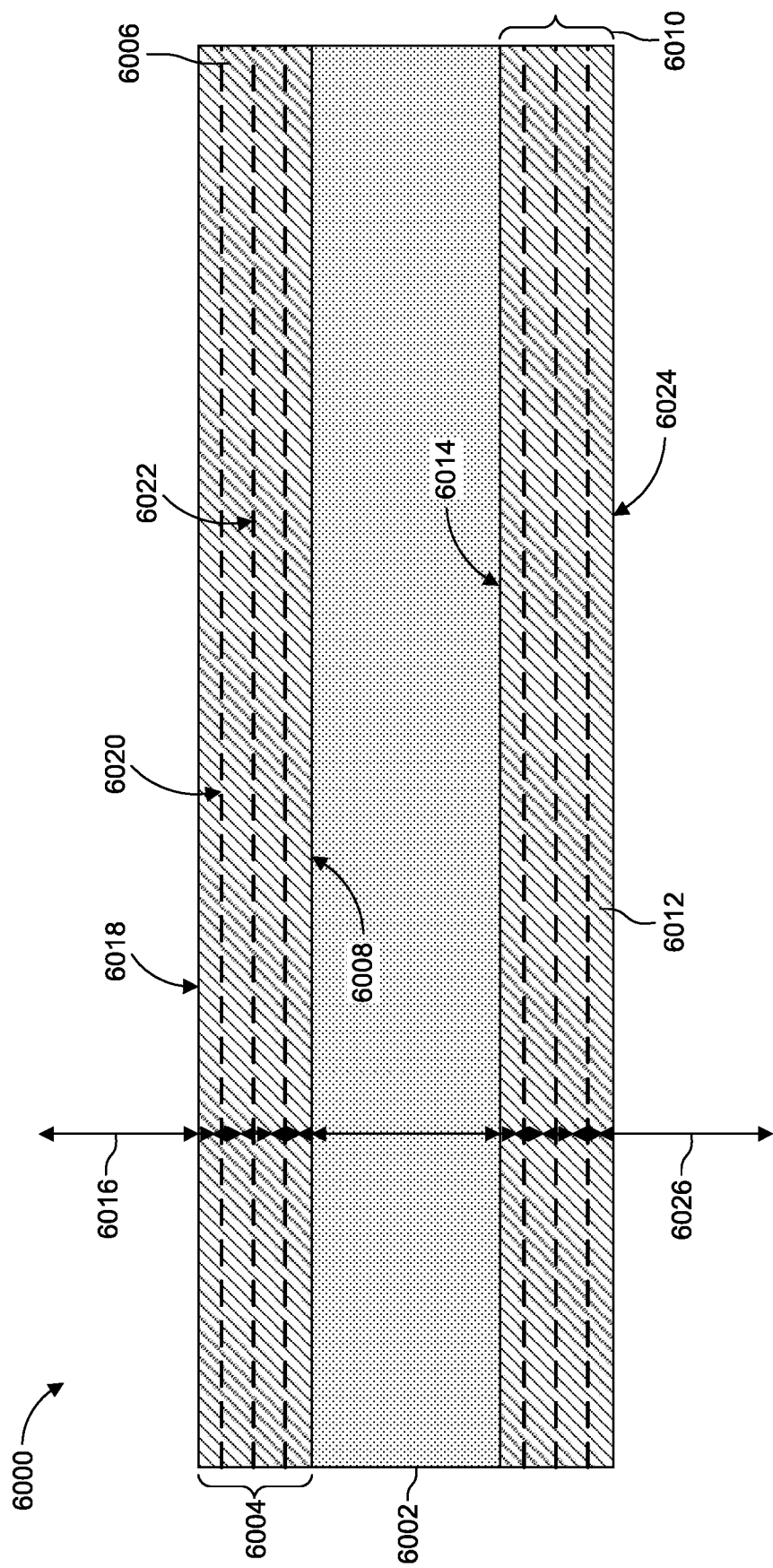
FIG. 6 is a cross section of a filter suitable for use in the lighting apparatus of FIG. 1, according to an embodiment.

FIG. 6 is a cross-section of an optical filter 6000, which is suitable for use as the filter 1010 in the lighting apparatus 1000 of FIG. 1, according to an embodiment.

In an embodiment, the filter 6000 is a thin-film dichroic filter including a substrate 6002, a first set 6004 of one or more layers 6006 disposed over a side 6008 of the substrate, and an optional second set 6010 of one or more layers 6012 disposed over another side 6014 of the substrate.

The substrate 6002 can be made from any suitable ultraviolet transmitting material such as a ultraviolet glass. For example, the substrate 6002 can be a high-purity fused-silica substrate such as a Corning HPFS 7980 grade 5f substrate.

Each layer 6006 of the first set 6004 of one or more layers is vacuum deposited hafnium oxide or silicon oxide (or silicon dioxide), or a combination of both hafnium oxide and silicon oxide. For example, the first set 6004 of one or more layers 6006 can include multiple layers 6006 that alternate between hafnium oxide and silicon oxide. Further in example, the first set 6004 of one or more layers includes up to sixty total layers 6006, which collectively have a thickness of approximately ten microns. As described below, the thickness of each layer 6006 can be set to impart desired filtering properties or characteristics to the filter 6000.

The second set 6010 of one or more layers 6012, if included, can be the same as, or similar to, the first set 6004 of one or more layers 6006. For example, each layer 6012 of the second set 6010 is vacuum deposited hafnium oxide or silicon oxide (or silicon dioxide), or a combination of both hafnium oxide and silicon oxide. Further in example, the second set 6010 of one or more layers can include multiple layers 6012 that alternate between hafnium oxide and silicon oxide. Still further in example, the second set 6010 of one or more layers 6012 includes sixty total layers 6012, which collectively have a thickness of approximately ten microns. As described below, the thickness of each layer 6012 can be set to impart desired filtering properties or characteristics to the filter 6000.

As described below, the filter 6000 has improved characteristics as compared to conventional optical filters such as the glass color filters described above in conjunction with FIGS. 3-5. For example, as compared to conventional optical filters, the thin-film dichroic filter 6000 has a higher transmissivity at at least a primary ultraviolet wavelengths approximately 253.7 nanometers, a lower transmissivity at least at one of the visible wavelengths such as 405 nanometers, and experiences a lower level of solarization—the wavelength of approximately 253.7 nanometers can be a primary ultraviolet wavelength, because, e.g., this is the highest-intensity, or the only, ultraviolet wavelength generated by the lamp 1008 (or another lamp), or because this wavelength otherwise has been chosen as the dominant ultraviolet wavelength for fluorescing the fluorescent minerals.

Still referring to FIG. 6, below is a high-level description of the operation of the thin-film dichroic filter 6000. For purposes of this description, all layers 6006 and 6012, and surfaces of and interfaces between the layers, are assumed to be flat; although perfect flatness may be desired, in reality the layers, surfaces of the layers, or interfaces between the layers, may not be perfectly flat.

A ray 6016 of multiwavelength light is incident on, and normal to (incident at an angle of incidence equal to 0°), the outermost layer 6006 of the layer set 6004. A surface 6018 of the outermost layer 6006 redirects a first redirected portion of the ray 6016 back along the path of the incident ray, and a first remaining portion of the ray propagates through the outermost layer to, and is incident on, an interface 6020 between the outermost layer 6006 and the second outermost layer 6006. The first redirected portion of the ray 6016 interferes with the incident ray 6016, and at one or more wavelengths the interference is constructive and at one or more other wavelengths the interference is destructive. The interface 6020 redirects a second redirected portion of the ray 6016 along the path of the first remaining portion of the ray, and a second remaining portion of the ray 6016 propagates through the second outermost layer 6006 and is incident on an interface 6022 between the second outermost layer and a third outmost layer 6006. The second redirected portion of the ray 6016 interferes with the first remaining portion of the ray 6016, the first redirected portion of the ray, and the incident ray, and at one or more wavelengths the interference is constructive and at one or more other wavelengths the interference is destructive.

A similar pattern of constructive and destructive interference occurs corresponding to the remaining layers 6006 and interfaces between those layers, the interface 6008 between the substrate 6002 and the inner-most layer 6006, the substrate, the interface 6014 between the substrate and the inner-most layer 6012, the layers 6012 and the interfaces between those layers, and a surface 6024 of the outermost layer 6012.

A final remaining portion 6026 of the ray 6016 includes only the one or more wavelengths that made it through the entire thickness of the filter 6000 by virtue of the filter's patterns of constructive and destructive interference.

The operation of the filter 6000 can be analyzed in a similar manner for multiwavelength rays that are incident on the surface 6018 at angles other than 0° (normal).

The wavelengths at which the filter 6000 causes constructive interference, and the other wavelengths at which the filter causes destructive interference, depend on the following filter parameters: the thickness of the substrate 6002, the respective thickness of each layer 6006 and 6012, the respective index of refraction of each of the substrate 6002 and the layers 6006 and 6012, the numbers of layers 6006 and 6012, and the angles of incidence of the incident rays (that is, the filter 6000 may have different filter characteristics for different angles of incidence of the incoming rays). By manipulating any one or more of these parameters, a filter designer can obtain the filter 6000 having desired characteristics.

Figure 7:
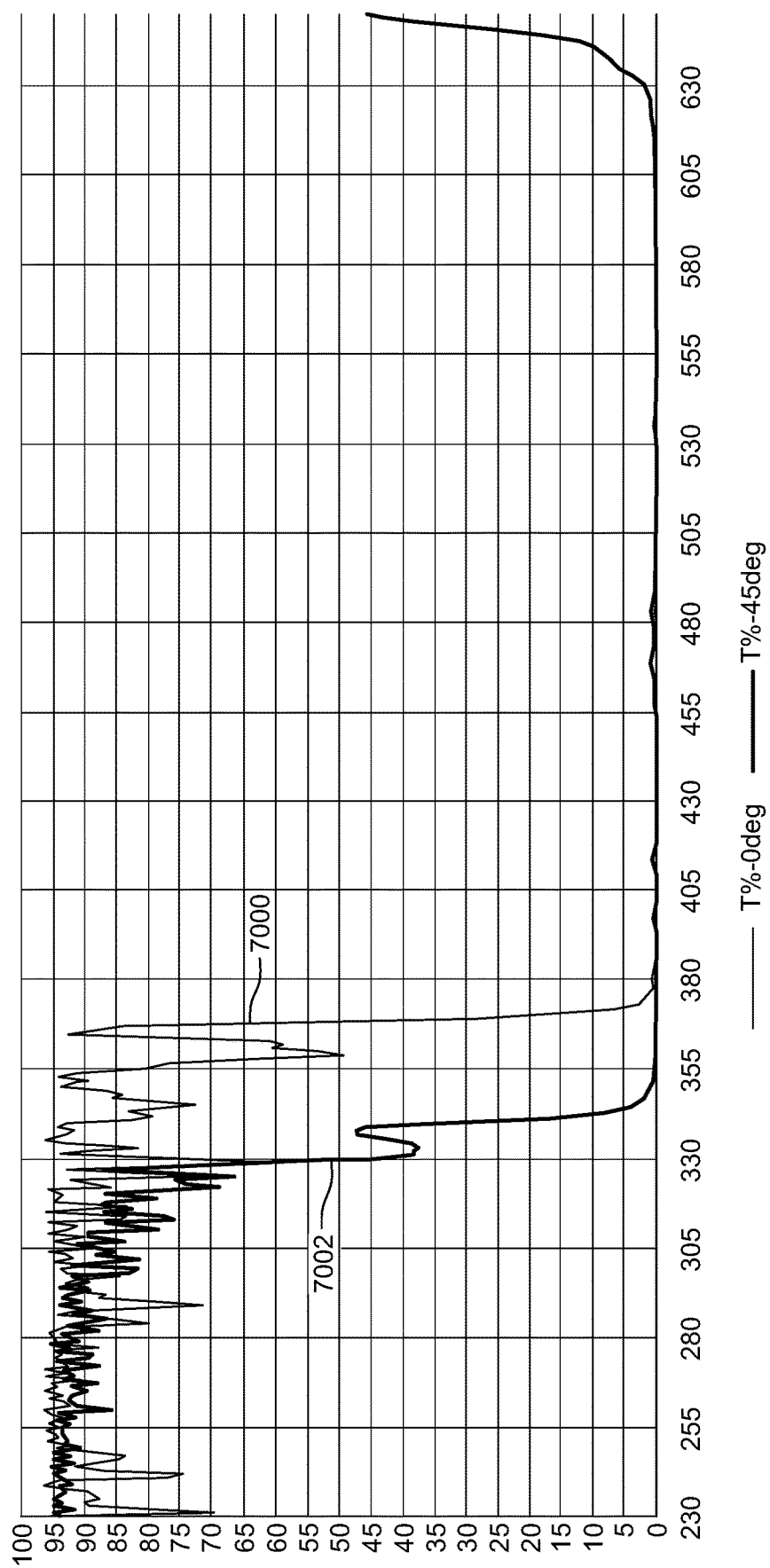
FIG. 7 is a plot of the transmissivity versus wavelength for the filter of FIG. 6 at angles of incidence of incoming electromagnetic radiation at 0° and 45°, according to an embodiment.

FIG. 7 is a plot including curves 7000 and 7002 of the transmissivity of the filter 6000 of FIG. 6 versus wavelength for respective angles of incidence 0° (normal) and 45°, according to an embodiment.

The curve 7000 shows that, at a 0° (normal) angle of incidence, the filter 6000 of FIG. 6 has a greater than 80% transmissivity (less than 20% attenuation) at each of one or more of the following wavelengths: approximately 253.7 nanometers (approximately 95% transmissivity in an embodiment), approximately 306 nanometers (approximately 90% transmissivity in an embodiment), approximately 312 nanometers (approximately 90% transmissivity in an embodiment), and approximately 365 nanometers (approximately 60% transmissivity in an embodiment), and, considering manufacturing tolerances, the filter is designed to have a transmissivity at each of one or more of these wavelengths of at least 70% (no more than 30% attenuation), and in other embodiments of at least 75% (no more than 20% attenuation), at least 82% (no more than 18% attenuation), at least 90% (no more than 10% attenuation), and at least 95% (no more than 5% attenuation).

And the curve 7002 shows that, at a 45° angle of incidence, the filter 6000 of FIG. 6 has a greater than 80% transmissivity (no more than 20% attenuation) at each of one or more of the following wavelengths: approximately 253.7 nanometers (approximately 92.5% transmissivity in an embodiment), approximately 306 nanometers (approximately 87.5% transmissivity in an embodiment), approximately 312 nanometers (approximately 75% transmissivity in an embodiment), and approximately 365 nanometers (approximately 0.5% transmissivity in an embodiment), and, considering manufacturing tolerances, the filter is designed to have a transmissivity at each of one or more of these wavelengths of at least 70% (no more than 30% attenuation), and in other embodiments of at least 75% (no more than 25% attenuation), at least 82% (no more than 18% attenuation), at least 90% (no more than 10% attenuation), and at least 95% (no more than 5% attenuation).

Furthermore, the curves 7000 and 7002 show that the filter 6000 of FIG. 6 has low transmissivities (high attenuations) at most visible wavelengths, including the visible emission lines at approximately 405 nanometers, 435 nanometers, 548 nanometers, 576 nanometers, and 579 nanometers that a mercury arc lamp can generate, according to an embodiment. For example, at approximately 405 nanometers, the filter 6000 has a transmissivity of less than 15% (attenuation of more than 85%) regardless of the angle of incidence of an incoming ray, transmissivity of less than 10% (attenuation of more than 90%), transmissivity less than 5% (attenuation of more than 95%), transmissivity less than 1% (attenuation of more than 99%), and transmissivity less than 0.5% (attenuation of more than 99.5%). And the filter 6000 has similar transmissivities and corresponding attenuations at approximately 435 nanometers, 548 nanometers, 576 nanometers, and 579 nanometers.

Figure 8:
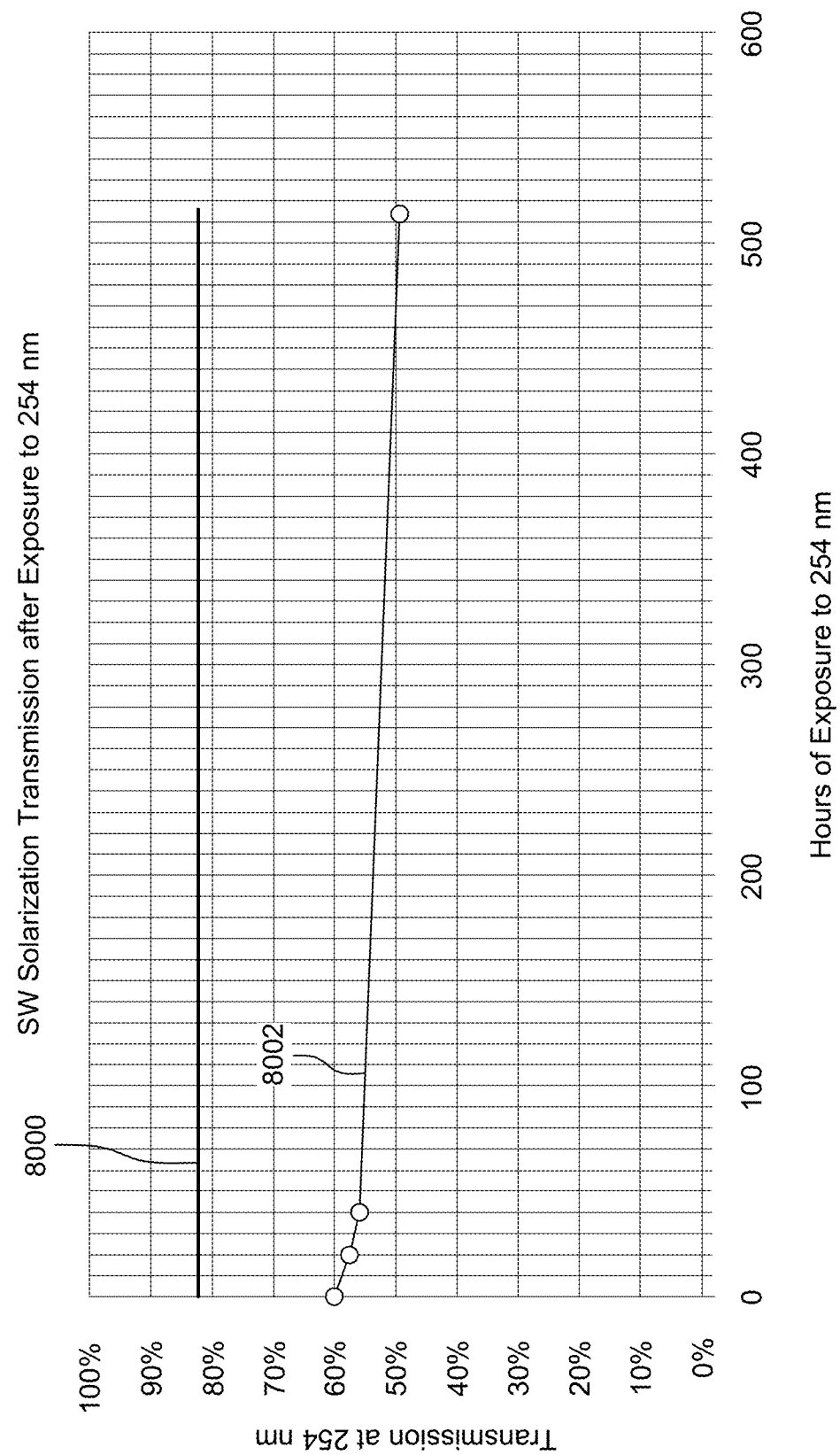
FIG. 8 is a plot of transmissivity versus time at approximately 254 nanometers for the filter of FIG. 1 having the transmissivity profile of FIG. 2 and for the filter of FIG. 6, according to an embodiment.

FIG. 8 is a plot including curves 8000 and 8002 of the transmissivity of an embodiment of the filter 6000 of FIG. 6 over time versus the transmissivity of a glass filter manufactured by Hoya over time, according to an embodiment in which the filter 6000 includes a Corning HPFS 7980 grade 5*f* substrate 6002, and includes one hundred twenty layers 6006 and 6012 on each side of the substrate, where the layers are vacuum deposited and made from one or more of hafnium oxide, silicon oxide, and a combination of hafnium oxide and silicon oxide.

Per the curve 8000, an embodiment of the filter 6000 experiences little to no solarization, and, therefore, maintains a transmissivity of approximately 82% at 253.7 nanometers for more than 500 hours of exposure to a wavelength at approximately 253.7 nanometers. The filter 6000 can experience a solarization similar to the solarization at approximately 253.7 nanometers for one or more of the following wavelengths: approximately 306 nanometers, approximately 312 nanometers, and approximately 365 nanometers.

In contrast, per the curve 8002, the glass filter experiences significant solarization after exposure to a wavelength of approximately 253.7 nanometers, and, therefore, has a transmissivity that drops from approximately 60% at 0 hours of exposure to a transmissivity of approximately 50% at 500 hours of exposure (a drop of more than 16%), and that continues to drop beyond 500 hours of exposure. The glass filter can experience a solarization similar to the solarization at approximately 253.7 nanometers for one or more of the following wavelengths: approximately 306 nanometers, approximately 312 nanometers, and approximately 365 nanometers.

Referring again to FIGS. 6-8, an embodiment of the thin-film dichroic filter 6000 that provides the filter characteristics described above in conjunction with FIGS. 7-8 includes a Corning HPFS 7980 grade 5f substrate 6002, and includes one hundred twenty layers 6006 and 6012 on each side 6008 and 6014, respectively, of the substrate, where the layers are vacuum deposited and made from one or more of hafnium oxide, silicon oxide, and a combination of hafnium oxide and silicon oxide. Furthermore, the thin-film dichroic filter 6000 has the same or similar filter characteristics regardless of whether the set 6004 of layers 6006 or the set 6010 of the layers 6012 are facing the lamp 1008.

Figure 9:
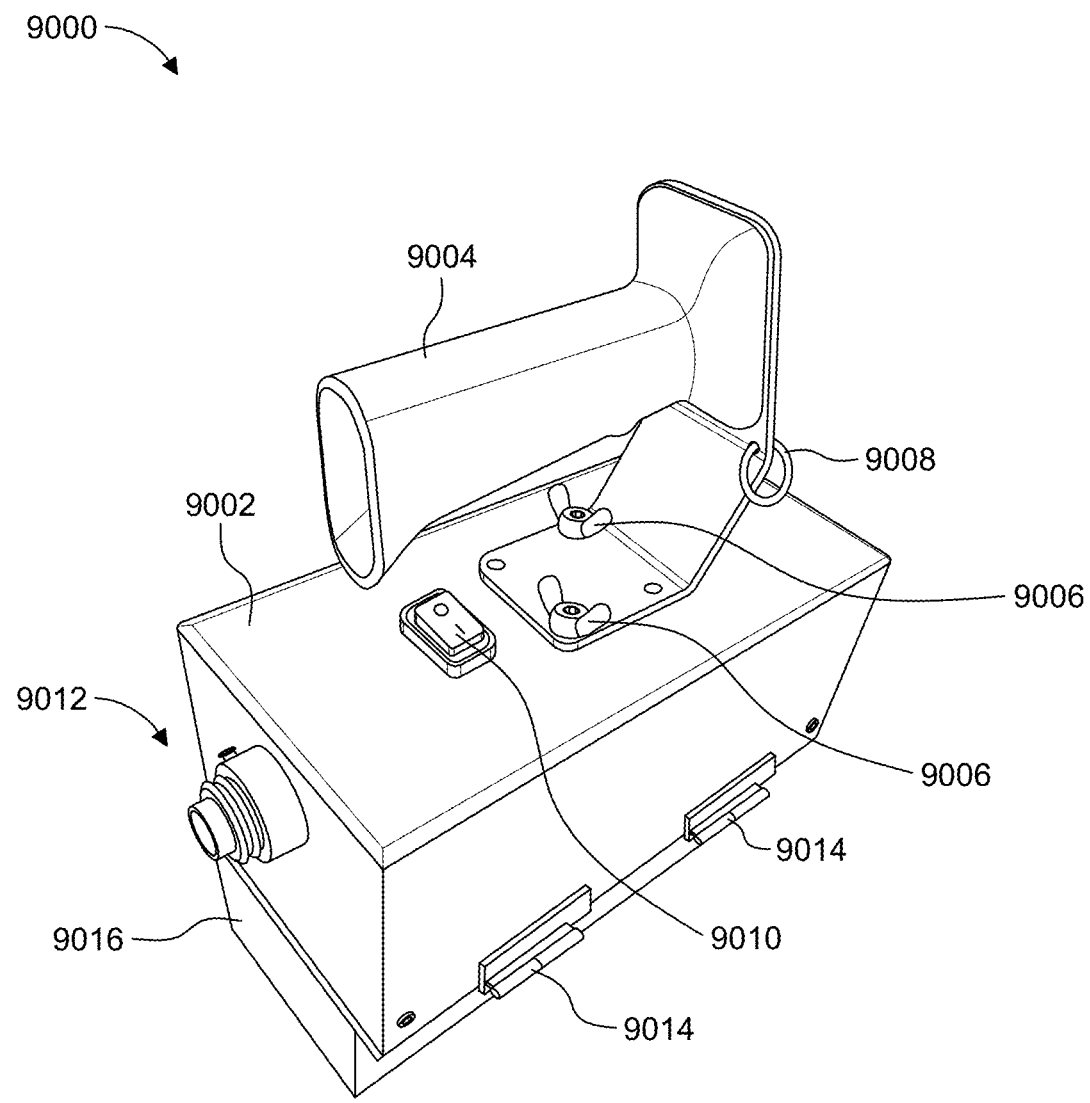
FIG. 9 is a top perspective view of a portable lighting apparatus that includes the filter of FIG. 6, according to an embodiment.

FIG. 9 is a top perspective view of a portable lighting apparatus 9000, which is generally configured according to the lighting apparatus 1000 of FIG. 1, according to an embodiment.

Figure 10:
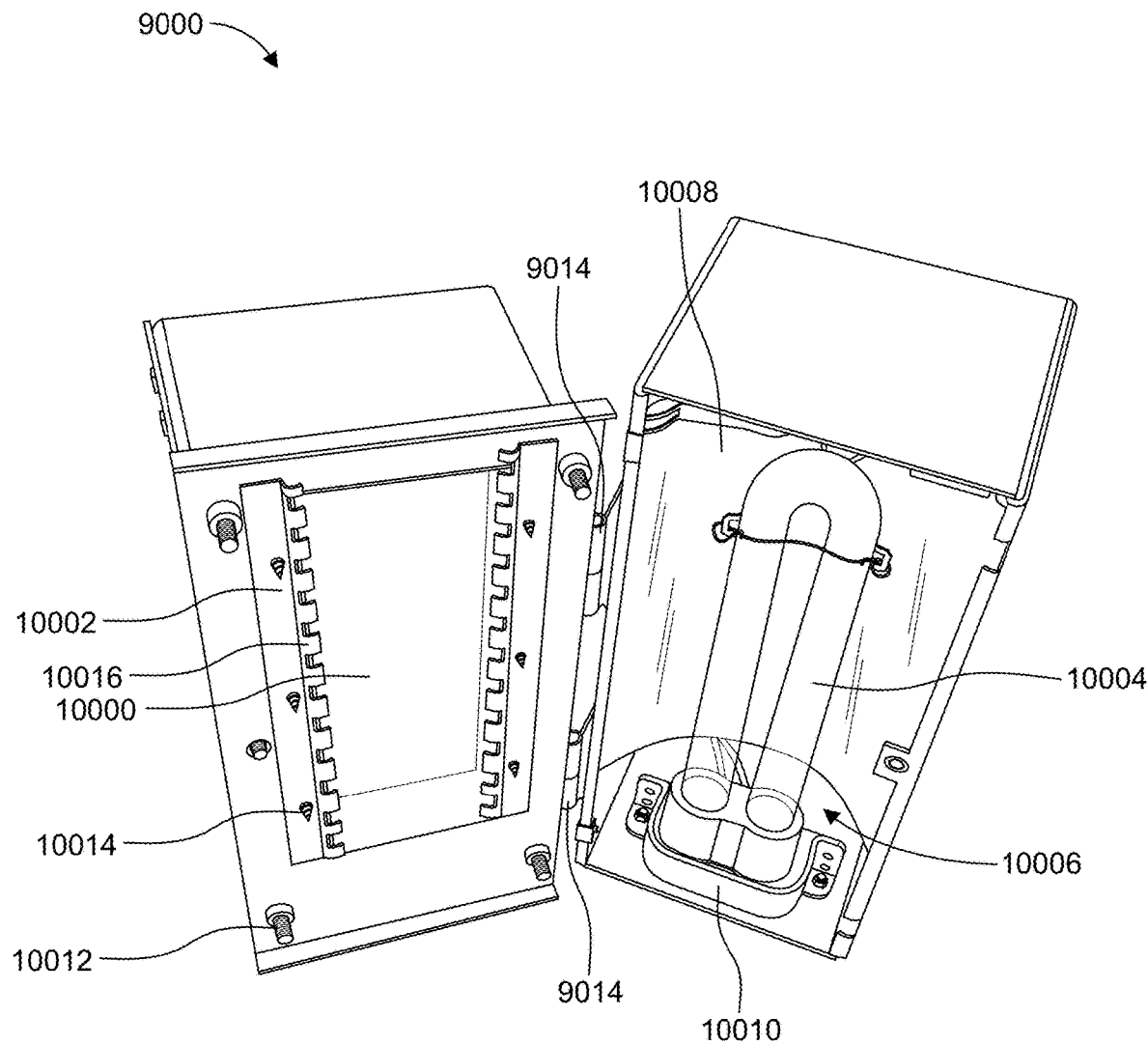
FIG. 10 is a bottom perspective view of the lighting apparatus of FIG. 9 in an open configuration, according to an embodiment.

FIG. 10 is an open perspective view of the portable lighting apparatus 9000, according to an embodiment.

Figure 11:
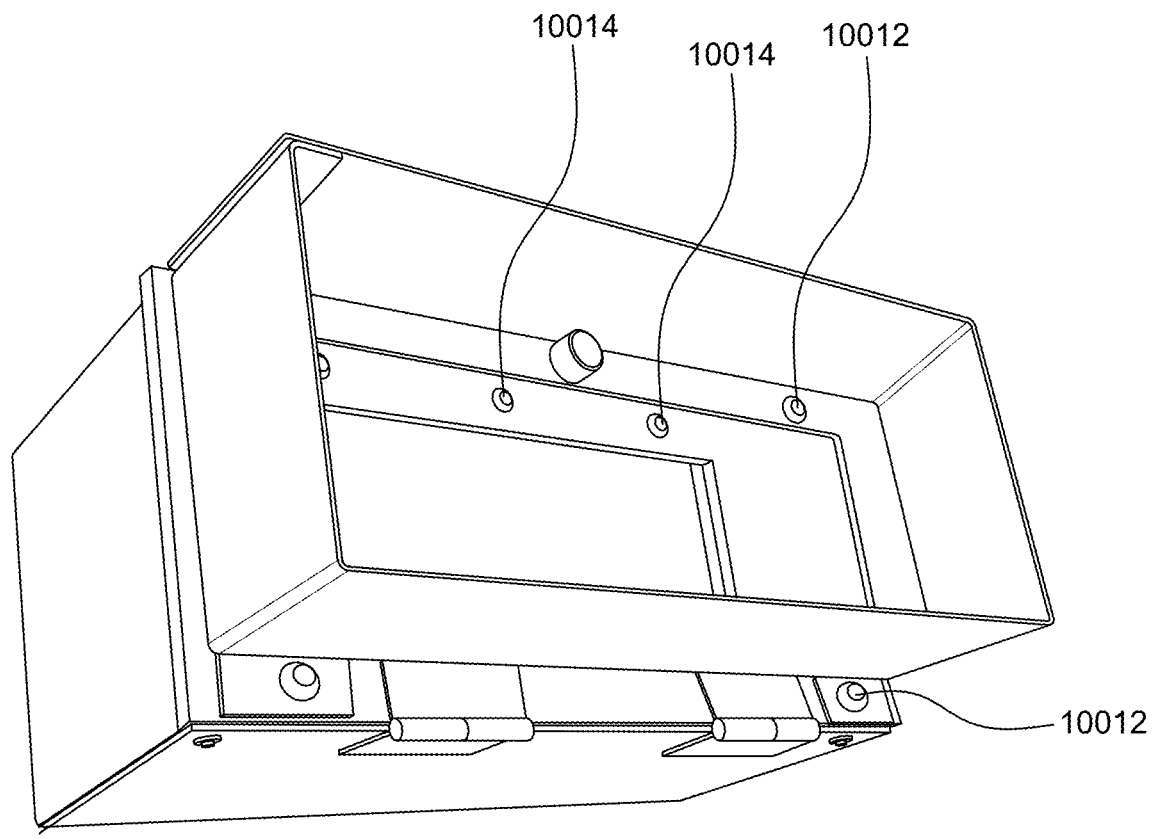
FIG. 11 is a bottom perspective view of the lighting apparatus of FIGS. 9 and 10 in a closed configuration, according to an embodiment.

FIG. 11 is a bottom perspective view of the portable lighting apparatus 9000, according to an embodiment.

Referring to FIGS. 9-11, the portable lighting apparatus 9000 is configured for use by fluorescent-mineral prospectors and hobbyists who would like to determine whether a prospected, or otherwise found, rock includes any exposed fluorescent minerals, or who would like to temporarily display one or more fluorescent minerals from their collections, according to an embodiment. For example, the portable lighting apparatus 9000 allows a prospector or hobbyist to determine whether prospected, or otherwise found, rocks include exposed fluorescent minerals without the need to haul the rocks back to a workshop to make such a determination.

Still referring to FIGS. 9-11, in an embodiment, the lighting apparatus 9000 includes a housing 9002, a handle 9004 attachable to the housing by wingnuts 9006, a ring connector 9008 for a lanyard (so that a user can carry the lighting apparatus around his/her neck), a power on/off switch 9010, a power-supply connector 9012, hinges 9014, a removable baffle 9016, a filter 10000, which may be the same as, or similar to, the filter 6000 described above in conjunction with FIGS. 6-8, a filter mount 10002, a mercury arc lamp 10004, which may be the same as, or similar to, the lamp 1008 described above in conjunction with FIG. 1 (the lamp 10004 also can be an ultraviolet LED), a cavity 10006 having a reflective surface 10008, which may be the same as, or similar to, the cavity 1004 and the reflective surface 1012 described above in conjunction with FIG. 1, a lamp socket 10010 (the lamp socket can be different if the lamp 10004 is an ultraviolet LED), a power supply (not shown in FIGS. 9-11) coupled to the power-supply connector and to the lamp socket, baffle-mounting screws 10012, and filter mounting screws 10014.

Although shown as being rectangular and being made from painted metal, the housing 9002 can have any suitable shape and can be made from any suitable material(s). For example, the dimensions of the housing can be approximately 4 inches wide, by 5.5 inches high by 8 inches long.

Although described as being made partially from plastic and partially from metal, and having a particular hand-grip shape, the handle 9004 can be made from any suitable material(s) and can have any suitable shape.

Furthermore, although described as being removably attachable to the housing 9002 with wing nuts 9006, the handle 9004 can be permanently attached to the housing by, e.g., welding or an adhesive.

In addition, one or more of the wingnuts 9006 can be replaced with any other suitable handle-attachment apparatuses such as bolts, screws, and thumbscrews.

The connector 9008 can be of any suitable construction and made from any suitable material(s).

The power on/off switch 9010 is configured to connect the lamp 10004 (via the lamp socket 10010) to an onboard power supply (not shown in FIGS. 9-11) in an "on" position or state, and is configured to disconnect the lamp form the power supply in an "off" position or state. For example, the power switch 9010 can be a push-button switch or a flip switch.

The power-supply connector 9012 is configured to connect to an external power source, such as the main power grid (e.g., 110-120 VAC, 60 Hz in the U.S.) via an outlet, or a portable power source such as a 12 VDC battery. In an embodiment where the power connector 9012 is configured to connect to the main power grid, the lighting apparatus 9000 can come with, or otherwise can be compatible with, an external (to the housing 9002) power adapter configured to convert a main-power-grid voltage (e.g., 100-240 VAC, 50 or 60 Hz) into a voltage, such as 12 VDC, with which the lighting apparatus is configured to use to power the lamp 10008 and other electronic components and devices (not shown in FIGS. 9-11) onboard the lighting apparatus 9000. Alternatively, the power connector 9012 can be configured to connect directly to a main-power-grid voltage (e.g., via a wall outlet or a generator outlet), and the onboard power supply (not shown in FIGS. 9-11) can be configured to covert the main-power-grid voltage into a voltage suitable for driving the lamp 10004 and other electronic components and devices onboard the lighting apparatus.

The hinges 9014 can be any apparatus suitable to allow one to open the lighting apparatus 9000, for example, to clean or to replace the filter 10000 or the lamp 10004, or to repair or to replace the reflective surface 10008 of the cavity 10006, the lamp socket 10010, the power-supply connector 9012, the internal power supply (not shown in FIGS. 9-11), or any other component partially or fully internal to the lighting apparatus. Although the lighting apparatus 9000 is described as including two hinges, the lighting apparatus can include fewer or more than two hinges.

The removable baffle 9016 is configured to prevent one or more visible wavelengths of electromagnetic energy generated by the lamp 10004 and that form rays that pass through the filter 10000, for example, at an angle other than 0° (normal)—as described above, the filter can have different transmissivity/attenuation characteristics for rays from the lamp 10004 that are incident on the filter at 0° as compared to rays from the lamp that are incident on the filter at other angles. For example, the baffle 9016 can be anodized, painted, or otherwise colored with black such that the baffle is a poor redirector of electromagnetic radiation. Further in example, if the filter 10000 is configured to suitably attenuate all visible wavelengths generated from lamp rays that are incident on the filter 1000 at an angle of 0°, then one can assume that only visible wavelengths generated from lamp rays incident on the filter surface at non-zero angles can have insufficient attenuation to prevent these visible rays from degrading the visual appeal of one or more fluorescing minerals. It is these visible rays that the baffle 9016 is configured to block from the view of a viewer of the one or more fluorescing minerals. And the depth of the baffle 9016 can be within a range of approximately 9 millimeters to approximately 12 millimeters.

The filter 10000 can be the same as, or similar to, the filter 6000 of FIG. 6. Furthermore, the filter 10000 can include an edge or boundary region suitable to engage the filter mount 10002.

The filter mount 10002 includes prongs 10016, which are configured to engage the filter 10000 and are rounded, or have another shape, suitable so that the prongs impart few, if any, markings (e.g., scratches, scuffs) to the filter. Furthermore, the filter mount 10002 can be made from any suitable material such as aluminum, another metal, or plastic.

The lamp 10004, which can be the same as, or similar to, the mercury arc lamp 1004 described above in conjunction with FIG. 1, can be any suitable mercury arc lamp, or can be any other type of suitable lamp (a lamp that can generate a suitably powerful emission line at one or more of the following wavelengths: approximately 253.7 nanometers (this wavelength may be the primary ultraviolet wavelength), approximately 306 nanometers, approximately 312 nanometers, and approximately 365 nanometers) such as an ultraviolet fluorescent-tube lamp or an ultraviolet LED.

The cavity 10006 can be formed in any suitable material, such as an injection-molded piece of plastic or can be formed by a curved piece of aluminum, and the reflective surface 10008 can be the cavity-defining wall or surface of the material itself, or one can coat the cavity-defining surface with a reflective material such as aluminum, aluminum-coated glass, or a Bragg reflector.

The lamp socket 10010 can be any suitable socket or other apparatus in which one can removably mount the lamp 10004 in a manner that allows the lamp to be powered by the internal power supply (not shown in FIGS. 9-11).

The internal power supply (not shown in FIGS. 9-11) can be any power supply suitable for powering the lamp 10004 and any other electronic components (e.g., an indicator light-emitting diode (LED)) of the lighting apparatus 9000. Furthermore, the power supply may include other components such as a ballast.

And the baffle-mounting screws 10012 and the filter-mounting screws 10014 can be any suitable screws or other fasteners suitable for respectively removably mounting the baffle 9016 and the filter mount 10002 to the housing 9002.

Figure 12:
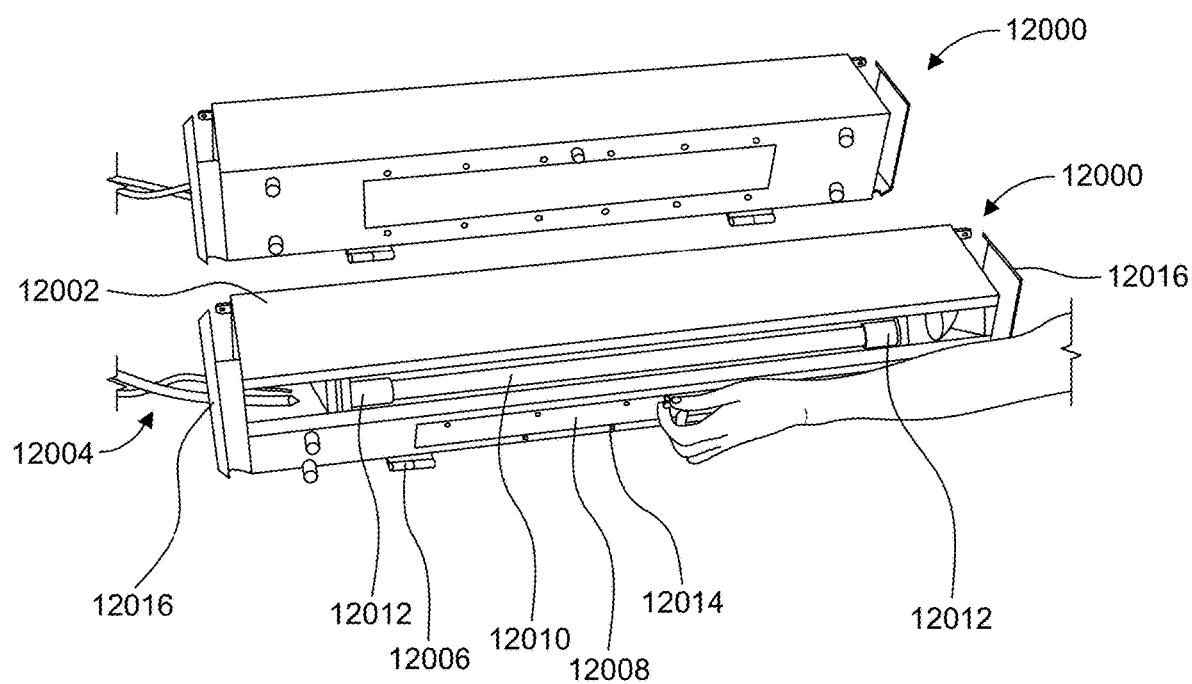
FIG. 12 is a perspective bottom-side view of a mountable lighting apparatus that includes the filter of FIG. 6 in a closed position (top of FIG. 12) and in an open position (bottom of FIG. 12), according to another embodiment.

FIG. 12 is a perspective view of two display lighting apparatuses 12000, which are configured for mounting as part of a fluorescent-mineral display and to generate and emit the electromagnetic radiation that causes one or more fluorescent minerals in the display to fluoresce, according to an embodiment. Described below is the structure and operation of one of the lighting apparatuses 12000, it being understood that the other one of the lighting apparatuses has a same or similar structure and operates in a same or similar manner.

In general, the lighting apparatus 12000 is the same as, or similar to, in structure and in operation, the lighting apparatus 9000 described above in conjunction with FIGS. 9-11, except that the lighting apparatus has different dimensions and is configured to be mounted within or otherwise adjacent to a fluorescent-mineral display such as the display 2000 described above in conjunction with FIG. 2.

In an embodiment, the lighting apparatus 12000 includes a housing 12002, a power on/off switch (not shown in FIG. 12), power-supply lines 12004, hinges 12006, a filter 12008, which may be the same as, or similar to, the filter 6000 described above in conjunction with FIGS. 6-8 or the filter 10000 described above in conjunction with FIGS. 9-11, a filter mount (not shown in FIG. 12), a mercury arc lamp 12010, which may be a straight version of the lamp 1008 described above in conjunction with FIG. 1 or a straight version of the lamp 10004 described above in conjunction with FIGS. 9-11 (also, one can substitute an ultraviolet LED for the mercury arc lamp 12010), a cavity (not shown in FIG. 12), with a reflective surface (not shown in FIG. 12), which may be the same as, or similar to, the cavity 1004 and the reflective surface 1012 described above in conjunction with FIG. 1 or the same as, or similar to, the cavity 10006 and the reflective surface 10008 described above in conjunction with FIGS. 9-11, lamp sockets 12012, an internal power supply (not shown in FIG. 12), which is coupled to the power-supply lines 12004 and which may be the same as, or similar to, the internal power supply of the lighting apparatuses 1000 and 9000 of FIGS. 1 and 9, filter mounting screws 12014, which may be the same as, or similar to, the filter mounting screws 10014 of FIGS. 9-11, and lighting-apparatus mounting brackets 12016.

Although shown as being rectangular and being made from painted metal, the housing 12002 can have any suitable shape, can be made from any suitable material(s), and can be coated with any suitable materials. For example, the dimensions of the housing can be in the range of approximately 33 inches long by approximately 5 inches wide by approximately 6 inches high.

The power-supply lines 12004 can be of any suitable construction and made from any suitable material(s) such as copper or aluminum, and can be configured to couple the lighting apparatus 12000 to a main power grid, such as a U.S. compatible grid that provides 110-120 VAC at 60 Hz or a Europe compatible grid that provides 220-240 VAC at 50 Hz.

The power on/off switch (not shown in FIG. 12) is configured to couple the lamp 12010 to an onboard power supply (not shown in FIG. 12) in an "on" position or state, and to uncouple the lamp form the power supply in an "off" position or state. For example, the power switch may be a push-button switch or a flip switch, or can be the same as, or similar to, the power on/off switch 9010 described above in conjunction with FIGS. 9-11.

The hinges 12006 can be any apparatus suitable to allow one to open the lighting apparatus 12000, for example, to clean or to replace the filter 12008 or the lamp 12010 or to repair or to replace the reflective surface (not shown in FIG. 12) of the cavity (not shown in FIG. 12), the lamp socket 12012, the power-supply lines 12004, the internal power supply (not shown in FIG. 12), or any other component partially or fully internal to the lighting apparatus. Although the lighting apparatus 12000 is described as including two hinges, the lighting apparatus can include fewer or more than two hinges.

The filter 12008 can be the same as, or similar to, the filter 6000 of FIG. 6 or the filter 10000 of FIGS. 9-11. Furthermore, the filter 12008 can include an edge or boundary (not shown in FIG. 12) to engage the prongs of the filter mount (not shown in FIG. 12).

The filter mount (not shown in FIG. 12) can be the same as, or similar to, the filter mount 10002 described above in conjunction with FIGS. 9-11, and can include prongs (not shown in FIG. 12) that are configured to engage the filter 12008 and that are rounded, or have another shape, suitable so that the prongs impart few, if any, marks (e.g., scratches, scuffs) to the filter. Furthermore, the filter mount can be made from any suitable material such as aluminum, another metal, or plastic.

The lamp 12010, which can be the same as, or similar to, the mercury arc lamp 1004 described above in conjunction with FIG. 1 or the mercury arc lamp 10004 described above in conjunction with FIGS. 9-11, can be any suitable mercury arc lamp, or can be any other type of suitable lamp (a lamp that can generate a suitably powerful emission line at each of one or more of the following wavelengths: approximately 253.7 nanometers (this wavelength may be the primary ultraviolet wavelength), approximately 306 nanometers, approximately 312 nanometers, and approximately 365 nanometers). For example, the lamp 12010 can be a straight mercury lamp instead of a curved mercury arc lamp like the lamps 1004 and 10004, or can be a UV LED.

The cavity (not shown in FIG. 12), which can be the same as, or similar to, the cavity 1004 described above in conjunction with FIG. 1 or to the cavity 10006 described above in conjunction with FIGS. 9-11, can be formed in any suitable material, such as in an injection-molded piece of plastic or by a curved piece of aluminum, and the reflective surface (not shown in FIG. 12) of the inner cavity wall can be the surface of the material in which the cavity is disposed, or one can coat the material wall that defines the cavity with a reflective material such as aluminum, aluminum-coated glass, or a Bragg reflector tuned, for example, to one or more of the following wavelengths: approximately 253.7 nanometers, approximately 306 nanometers, approximately 312 nanometers, and approximately 365 nanometers.

The lamp socket 12012, which can be the same as, or similar to, the lamp socket 10010 described above in conjunction with FIGS. 9-11, can be any suitable socket or other apparatus that is coupled to the internal power supply, in which one can removably mount the lamp 12010, and that can provide power to the lamp. For example, where the lamp 12010 is straight, the socket 10010 can have two socket ports on either side of the housing 12002, one port for each end of the lamp, as shown in FIG. 12.

The internal power supply (not shown in FIG. 12) can be the same as, or similar to, the power supply described above in conjunction with FIGS. 9-11, or can be any power supply suitable for powering the lamp 12010 and any other electronic components (e.g., an indicator light-emitting diode (LED)) of the lighting apparatus 12000. Furthermore, the power supply may include other components such as a ballast.

The filter-mounting screws 12014 can be any suitable screws or other fasteners suitable for removably mounting the filter mount (not shown in FIG. 12) to the hinged portion of the housing 12002.

And the mounting brackets 12016 can be any brackets or other apparatus suitable for removably mounting the housing 12002 to a wall, a display case, or other mounting member within, or otherwise associated with, a fluorescent-mineral display such as the display 2000 described above in conjunction with FIG. 2.

Although the features and elements of the disclosed subject matter are described in embodiments in particular combinations, each feature or element may be used alone without the other features and elements of the embodiments or in various combinations with or without other features and elements of the disclosed subject matter. For example, glass filters may have significant transmissivities at approximately 405 nanometers and/or 435 nanometers; because these wavelengths are at blue hues, one or both wavelengths may mix with ambient red light (or red light from fluorescing minerals) to generate visible pink light. If one wishes to generate a same or similar pink light with the filter 6000 of FIG. 6, the filter 10000 of FIGS. 9-11, or the filter 12008 of FIG. 12, one can adjust the filter characteristics to have a transmissivity at one or both of approximately 405 nanometers and approximately 435 nanometers suitable to generate such visible pink light.

What is claimed:

1. A lighting apparatus, comprising:
   a housing having a cavity with an opening;
   a lamp disposed within the cavity and configured to emit electromagnetic radiation at wavelengths of approximately 253.7 nanometers and of approximately 405 nanometers; and
   a filter mounted adjacent to the opening and configured to pass the emitted electromagnetic radiation at the wavelength of approximately 253.7 nanometers with a transmissivity of at least approximately 70% and at the wavelength of approximately 405 nanometers with a transmissivity of no more than approximately 5%.

2. The lighting apparatus of claim 1 wherein the transmissivity of the filter at the wavelength of approximately 253.7 nanometers drops no more than 10% after the filter has been exposed, cumulatively, to the wavelength of approximately 253.7 nanometers for up to one hundred hours.

3. The lighting apparatus of claim 1 wherein the transmissivity of the filter at the wavelength of approximately 253.7 nanometers drops no more than 10% after the filter has been exposed, cumulatively, to the wavelength of approximately 253.7 nanometers for up to five hundred hours.

4. The lighting apparatus of claim 1 wherein the filter is configured to have a transmissivity of at least 70% at the wavelength of approximately 253.7 nanometers for at least five-hundred hours.

5. The lighting apparatus of claim 1 wherein the filter is configured to have a transmissivity of at least 80% at the wavelength of approximately 253.7 nanometers.

6. The lighting apparatus of claim 1 wherein the filter is configured to have a transmissivity of at least 80% at the wavelength of approximately 253.7 nanometers for at least five-hundred hours.

7. The lighting apparatus of claim 1 wherein the filter is configured to have a transmissivity of no more than 5% at one or more of the following wavelengths: approximately 435 nanometers, approximately 548 nanometers, approximately 576 nanometers, and approximately 579 nanometers.

8. The lighting apparatus of claim 1 wherein the filter comprises:
   a substrate having a cavity-facing side and an outward-facing side, the cavity-facing side configured to receive electromagnetic radiation emitted from the lamp; and
   a layer of material disposed over one of the cavity-facing side and the outward-facing side of the substrate and including sublayers each configured to pass a respective passed portion of the received electromagnetic radiation, each of at least one interface between contiguous ones of the sublayers configured to redirect a portion of a respective passed portion such that the respective redirected portion interferes with at least one respective passed portion of the electromagnetic radiation.

9. The lighting apparatus of claim 8 wherein the substrate includes high-purity fused silica.

10. The lighting apparatus of claim 8 wherein at least one of the sublayers includes hafnium oxide and wherein at least another one of the sublayers includes silicon oxide.

11. The lighting of claim 8 wherein the layer has a thickness of no more than approximately ten microns.

12. The lighting apparatus of claim 1 wherein the filter comprises:
a substrate having a cavity-facing side and an outward-facing side, the cavity-facing side configured to receive electromagnetic radiation emitted from the lamp; and
two layers of material each disposed over a respective one of the cavity-facing side and the outward-facing side of the substrate and including sublayers each configured to pass a respective portion of the received electromagnetic radiation, each of at least one interface between contiguous ones of the sublayers configured to redirect a portion of a respective passed portion such that the respective redirected portion interferes with at least one respective passed portion of the electromagnetic radiation.

13. The lighting apparatus of claim 1 wherein the lamp includes a mercury arc lamp or an ultraviolet LED.

14. The lighting apparatus of claim 1 wherein the cavity includes a reflector configured to redirect, toward the filter, electromagnetic radiation emitted by the lamp and incident on the reflector.

15. The lighting apparatus of claim 1 wherein the lamp is configured to emit electromagnetic radiation at one or more of the following wavelengths: approximately 306 nanometers, approximately 312 nanometers, and approximately 365 nanometers.

16. A method, comprising:
generating electromagnetic radiation at wavelengths of approximately 253.7 nanometers and of approximately 405 nanometers;
attenuating, with a filter, the electromagnetic radiation at the wavelength of approximately 253.7 nanometers by no more than 30%; and
attenuating, with the filter, the generated electromagnetic radiation at the wavelength of approximately 405 nanometers by no less than 95%.

17. The method of claim 16 wherein the attenuation of the filter at the wavelength of approximately 253.7 nanometers increases no more than 10% after the filter has been exposed, to the wavelength of approximately 253.7 nanometers for at least one hundred hours.

18. The method of claim 16 wherein attenuating the electromagnetic radiation at the wavelength of approximately 253.7 nanometers includes attenuating the electromagnetic radiation at the wavelength of approximately 253.7 nanometers by no more than 20%.

19. The method of claim 16 wherein:
generating includes generating the electromagnetic radiation at wavelengths of, approximately 435 nanometers, approximately 548 nanometers, approximately 576 nanometers, and approximately 579 nanometers; and
attenuating the electromagnetic radiation at each of the wavelengths of, approximately 435 nanometers, approximately 548 nanometers, approximately 576 nanometers, and approximately 579 nanometers by no less than 95%.

20. The method of claim 16, further comprising illuminating an item with the attenuated electromagnetic radiation.

21. The method of claim 16, further comprising fluorescing a fluorescent mineral with the attenuated electromagnetic radiation.

22. The method of claim 16, further comprising:
generating electromagnetic radiation at one or more of the following wavelengths: approximately 306 nanometers, approximately 312 nanometers, and approximately 365 nanometers; and
attenuating, with a filter, the electromagnetic radiation at the one or more wavelengths by no more than 30%.

* * * * *